United States Patent [19]

Wilkinson et al.

[11] Patent Number: 5,799,507
[45] Date of Patent: Sep. 1, 1998

[54] HYDROCARBON GAS PROCESSING

[75] Inventors: John D. Wilkinson; Hank M. Hudson; Kyle T. Cuellar, all of Midland, Tex.

[73] Assignee: Elcor Corporation, Dallas, Tex.

[21] Appl. No.: 738,321

[22] Filed: Oct. 25, 1996

[51] Int. Cl.⁶ ......................................................... F25J 3/06
[52] U.S. Cl. ................................................ 62/621; 62/619
[58] Field of Search ......................................... 62/621, 619

[56] References Cited

U.S. PATENT DOCUMENTS

| | | |
|---|---|---|
| Re. 33,408 | 10/1990 | Khan et al. . |
| 4,157,904 | 6/1979 | Campbell et al. ................. 62/621 |
| 4,171,964 | 10/1979 | Campbell et al. . |
| 4,251,249 | 2/1981 | Gulsby . |
| 4,278,457 | 7/1981 | Campbell et al. ................. 62/621 |
| 4,519,824 | 5/1985 | Huebel . |
| 4,617,039 | 10/1986 | Buck . |
| 4,687,499 | 8/1987 | Aghili ............................... 62/621 |
| 4,690,702 | 9/1987 | Paradowski et al. . |
| 4,854,955 | 8/1989 | Campbell et al. . |
| 4,869,740 | 9/1989 | Campbell et al. . |
| 4,889,545 | 12/1989 | Campbell et al. . |
| 4,895,584 | 1/1990 | Buck et al. ........................ 62/621 |
| 5,275,005 | 1/1994 | Campbell et al. . |

*Primary Examiner*—Ronald C. Capossel
*Attorney, Agent, or Firm*—Brumbaugh, Graves, Donohue & Raymond

[57] ABSTRACT

A process for the recovery of propane, propylene and heavier hydrocarbon components from a hydrocarbon gas stream is disclosed. The stream is cooled and/or expanded to partially condense it, then separated to provide one or more $C_3$ containing liquid steams and a first vapor stream. These streams are then directed into a distillation column wherein a second vapor stream is separated to recover a product containing the major portion of the $C_3$ components and heavier hydrocarbon components. A distillation stream is withdrawn from the column below the feed point of the first vapor stream and is then directed into heat exchange relation with the second vapor stream to cool the distillation stream and condense at least a part of it, forming a condensed stream. At least a portion of the condensed stream is directed to the distillation column as its top feed. The quantities and temperatures of the feeds to the distillation column are effective to maintain the overhead temperature of the distillation column at a temperature whereby the major portion of the desired components is recovered.

8 Claims, 6 Drawing Sheets

HYDROCARBON GAS PROCESSING

BACKGROUND OF THE INVENTION

This invention relates to a process for the separation of a gas containing hydrocarbons.

Propylene, propane and/or heavier hydrocarbons can be recovered from a variety of gases, such as natural gas, refinery gas, and synthetic gas streams obtained from other hydrocarbon materials such as coal, crude oil, naphtha, oil shale, tar sands, and lignite. Natural gas usually has a major proportion of methane and ethane, i.e., methane and ethane together comprise at least 50 mole percent of the gas. The gas also contains relatively lesser amounts of heavier hydrocarbons such as propane, butanes, pentanes and the like, as well as hydrogen, nitrogen, carbon dioxide and other gases.

The present invention is generally concerned with the recovery of propylene, propane and heavier hydrocarbons from such gas streams. A typical analysis of a gas stream to be processed in accordance with this invention would be, in approximate mole percent, 92.6% methane, 4.7% ethane and other $C_2$ components, 1.0% propane and other $C_3$ components, 0.2% iso-butane, 0.2% normal butane, 0.16% pentanes plus, with the balance made up of nitrogen and carbon dioxide. Sulfur containing gases are also sometimes present.

The historically cyclic fluctuations in the prices of both natural gas and its natural gas liquid (NGL) constituents have reduced the incremental value of propane and heavier components as liquid products. This has resulted in a demand for processes that can provide more efficient recoveries of these products. Available processes for separating these materials include those based upon cooling and refrigeration of gas, oil absorption, and refrigerated oil absorption. Additionally, cryogenic processes have become popular because of the availability of economical equipment that produces power while simultaneously expanding and extracting heat from the gas being processed. Depending upon the pressure of the gas source, the richness (ethane and heavier hydrocarbons content) of the gas, and the desired end products, each of these processes or a combination thereof may be employed.

The cryogenic expansion process is now generally preferred for propane recovery because it provides maximum simplicity with ease of start up, operating flexibility, good efficiency, safety, and good reliability. U.S. Pat. Nos. 4,157,904, 4,171,964, 4,251,249, 4,278,457, 4,519,824, 4,617,039, 4,687,499, 4,689,063, 4,690,702, 4,854,955, 4,869,740, 4,889,545, and 5,275,005, reissue U.S. Pat. No. 33,408, co-pending application No. 08/337,172 and co-pending application No. 08/696,114 describe relevant processes.

In a topic cryogenic expansion recovery process, a feed gas stream under pressure is cooled by heat exchange with other streams of the process and/or external sources of refrigeration such as a propane compression-refrigeration system. As the gas is cooled, liquids may be condensed and collected in one or more separators as high-pressure liquids containing some of the desired $C_3$+ components. Depending on the richness of the gas and the amount of liquids formed, the high-pressure liquids may be expanded to a lower pressure and fractionated. The vaporization occurring during expansion of the liquids results in further cooling of the stream. Under some conditions, pre-cooling the high pressure liquids prior to the expansion may be desirable in order to further lower the temperature resulting from the expansion. The expanded stream, comprising a mixture of liquid and vapor, is fractionated in a distillation (deethanizer) column. In the column, the expansion cooled stream(s) is (are) distilled to separate residual methane, ethane, nitrogen, and other volatile gases as overhead vapor from the desired $C_3$ components and heavier hydrocarbon components as bottom liquid product.

If the feed gas is not totally condensed (typically it is not), the vapor remaining from the partial condensation can be passed through a work expansion machine or engine, or an expansion valve, to a lower pressure at which additional liquids are condensed as a result of further cooling of the stream. The pressure after expansion is slightly below the pressure at which the distillation column is operated. The expanded stream then enters the lower section of an absorption column and is contacted with cold liquids to absorb the $C_3$ components and heavier components from the vapor portion of the expanded stream. The liquids from the absorption column are then pumped into the deethanizer column at an upper column feed position.

The overhead distillation stream from the deethanizer passes in heat exchange relation with the residue gas from the absorber column and is cooled, condensing at least a portion of the distillation stream from the deethanizer. The cooled distillation stream then enters the upper section of the absorption column where the cold liquids contained in the stream can contact the vapor portion of the expanded stream as described earlier. Typically, the vapor portion (if any) of the cooled distillation stream and the absorber overhead vapor combine in an upper separator section in the absorber column as residual methane and ethane product gas. Alternatively, the cooled distillation stream may be supplied to a separator to provide vapor and liquid streams. The vapor is combined with the absorber column overhead and the liquid is supplied to the absorber column as a top column feed.

The separation that takes place in this process (producing a residue gas leaving the process which contains substantially all of the methane and $C_2$ components in the feed gas with essentially none of the $C_3$ components and heavier hydrocarbon components, and a bottoms fraction leaving the deethanizer which contains substantially all of the $C_3$ components and heavier hydrocarbon components with essentially no methane, $C_2$ components or more volatile components) consumes energy for feed gas cooling, for reboiling the deethanizer, for refluxing the deethanizer, and/or for re-compressing the residue gas. The present invention provides a means for achieving this separation at substantially lower capital cost by allowing the absorption column and the deethanizer column to be combined into a single fractionation tower. In some cases, the present invention also provides an improvement in product recovery and/or a reduction in the utility requirements (cooling, reboiling, refluxing, and/or re-compressing) needed for the recovery of the desired products.

In accordance with the present invention, it has been found that $C_3$ recoveries in excess of 93 percent can be maintained while providing essentially complete rejection of $C_2$ components to the residue gas stream. In addition, the present invention makes possible essentially 100 percent separation of $C_2$ components and lighter components from the $C_3$ components and heavier hydrocarbon components at reduced energy requirements. The present invention, although applicable at lower pressures and warmer temperatures, is particularly advantageous when processing feed gases in the range of 400 to 800 psia or higher under conditions requiring column overhead temperatures of −50° F. or colder.

For a better understanding of the present invention, reference is made to the following examples and drawings. Referring to the drawings.

In the following explanation of the above figures, tables are provided summarizing flow rates calculated for representative process conditions. In the tables appearing herein, the values for flow rates (in pound moles per hour) have been rounded to the nearest whole number for convenience. The total stream rates shown in the tables include all nonhydrocarbon components and hence are generally larger than the sum of the stream flow rates for the hydrocarbon components. Temperatures indicated are approximate values rounded to the nearest degree. It should also be noted that the process design calculations performed for the purpose of comparing the processes depicted in the figures are based on the assumption of no heat leak from (or to) the surroundings to (or from) the process. The quality of commercially available insulating materials makes this a very reasonable assumption and one that is typically made by those skilled in the art.

DESCRIPTION OF THE PRIOR ART

Figure 1:
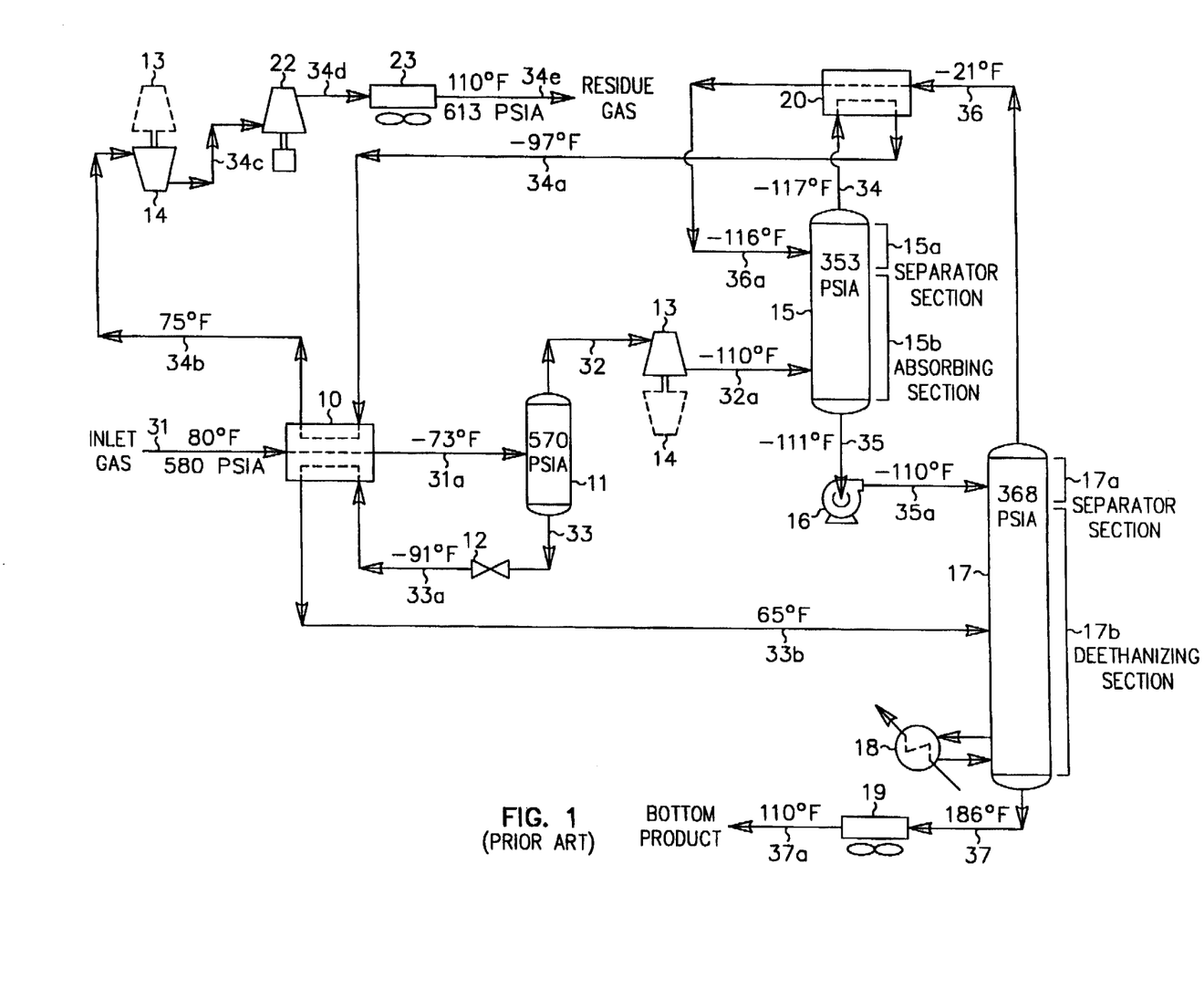
FIG. 1 is a flow diagram of a prior art cryogenic natural gas processing plant in accordance with U.S. Pat. No. 4,617,039.

Referring now to FIG. 1, in a simulation of the prior art process described therein, inlet gas enters the plant at 80° F. and 580 psia as stream 31. If the inlet gas contains a concentration of sulfur compounds which would prevent the product streams from meeting specifications, the sulfur compounds are removed by appropriate pretreatment of the feed gas (not illustrated). In addition, the feed stream is usually dehydrated to prevent hydrate (ice) formation under cryogenic conditions. Solid desiccant has typically been used for this purpose.

The feed stream 31 is cooled in exchanger 10 by heat exchange with cool residue gas at –97° F. (streams 34a) and with separator liquids at –91° F. (stream 33a). (The decision as to whether to use more than one heat exchanger for the indicated cooling services will depend on a number of factors including, but not limited to, inlet gas flow rate, heat exchanger size, stream temperatures, etc.). The cooled stream 31a enters separator 11 at –73° F. and 570 psia where the vapor (stream 32) is separated from the condensed liquid (stream 33).

The vapor (stream 32) from separator 11 enters a work expansion machine 13 in which mechanical energy is extracted from this portion of the high pressure feed. The machine 13 expands the vapor substantially isentropically from a pressure of about 570 psia to a pressure of about 353 psia, with the work expansion cooling the expanded stream 32a to a temperature of approximately –110° F. The expanded and partially condensed stream 32a is supplied to absorbing section 15b in a lower region of separator/absorber 15. The liquid portion of the expanded stream commingles with liquids falling downward from the absorbing section and the combined liquid stream 35 exits the bottom of separator/absorber 15 at –111° F. The vapor portion of the expanded stream rises upward through the absorbing section and is contacted with cold liquid falling downward to condense and absorb the propane and heavier components.

The separator/absorber tower 15 is a conventional distillation column containing a plurality of vertically spaced trays, one or more packed beds, or some combination of trays and packing. As is often the case in natural gas processing plants, the separator/absorber tower may consist of two sections. The upper section 15a is a separator wherein any vapor contained in the top feed is separated from its corresponding liquid portion, and wherein the vapor rising from the lower distillation or absorbing section 15b is combined with the vapor portion (if any) of the top feed to form the cold distillation stream 34 which exits the top of the tower. The lower, absorbing section 15b contains the trays and/or packing and provides the necessary contact between the liquids falling downward and the vapors rising upward to condense and absorb the propane and heavier components.

The combined liquid stream 35 from the bottom of the separator/absorber 15 is supplied as a cold top column feed (stream 35a) to deethanizer 17 by pump 16. The separator liquid (stream 33) is flash expanded to slightly above the 368 psia operating pressure of deethanizer 17 by expansion valve 12, cooling stream 33 to –91° F. (stream 33a) before it provides cooling to the incoming feed gas as described earlier. Stream 33b, now at 65° F., then enters deethanizer 17 at a mid-column feed point to be stripped of its methane and $C_2$ components.

The deethanizer in tower 17, operating at 368 psia, is also a conventional distillation column containing a plurality of vertically spaced trays, one or more packed beds, or some combination of trays and packing. The deethanizer tower may also consist of two sections: an upper section 17a wherein any vapor contained in the top feed is separated from its corresponding liquid portion, and wherein the vapor rising from the lower distillation or deethanizing section 17b is combined with the vapor portion (if any) of the top feed to form distillation stream 36 which exits the top of the tower; and a lower, deethanizing section 17b that contains the trays and/or packing to provide the necessary contact between the liquids falling downward and the vapors rising upward. The deethanizing section 17b also includes a reboiler 18 which heats and vaporizes a portion of the liquid at the bottom of the column to provide the stripping vapors which flow up the column to strip the liquid product, stream 37, of methane and $C_2$ components. A typical specification for the bottom liquid product is to have an ethane to propane ration of 0.02:1 on a molar basis. The liquid product stream 37 exits the bottom of the deethanizer at 186° F. and is cooled to 110° F. (stream 37a) in heat exchanger 19 before flowing to storage.

The operating pressure in deethanizer 17 is maintained slightly above the operating pressure of separator/absorber 15. This allows the deethanizer overhead vapor (stream 36) to pressure flow through heat exchanger 20 and thence into the upper section of separator/absorber 15. In heat exchanger 20, the deethanizer overhead at –21° F. is directed in heat exchange relation with the overhead (stream 34) from separator/absorber 15, cooling the stream to –116° F. (stream 36a) and partially condensing it. The partially condensed stream is then supplied to the separator section in separator/absorber tower 15, so that its condensed liquid is separated to become the cold liquid that contacts the vapors rising upward through the absorbing section.

The distillation stream leaving the top of separator/absorber 15 at −117° F. is the cold residue gas stream 34. The residue gas stream passes countercurrently to deethanizer overhead stream 36 in heat exchanger 20 and is warmed to −97° F. (stream 34a) as it provides cooling and partial condensation of the deethanizer overhead stream. The residue gas is further warmed to 75° F. (stream 34b) as it passes countercurrently to the incoming feed gas in heat exchanger 10. The residue gas is then re-compressed in two stages. The first stage is compressor 14 driven by expansion machine 13. The second stage is compressor 22 driven by a supplemental power source which compresses the residue gas (stream 34d) to sales line pressure. After cooling in discharge cooler 23, the residue gas product (stream 34e) flows to the sales gas pipeline at 110° F. and 613 psia.

A summary of stream flow rates and energy consumption for the process illustrated in FIG. 1 is set forth in the following table:

TABLE I (FIG. 1)
Stream Flow Summary - (Lb. Moles/Hr)

| Stream | Methane | Ethane | Propane | Butanes+ | Total |
|---|---|---|---|---|---|
| 31 | 81340 | 4128 | 878 | 439 | 87840 |
| 32 | 80476 | 3792 | 623 | 149 | 86078 |
| 33 | 864 | 336 | 255 | 290 | 1762 |
| 35 | 2199 | 1261 | 689 | 156 | 4359 |
| 36 | 3063 | 1581 | 121 | 7 | 4843 |
| 34 | 81340 | 4112 | 55 | 0 | 86562 |
| 37 | 0 | 16 | 823 | 439 | 1278 |

| Recoveries* | |
|---|---|
| Propane | 93.70% |
| Butanes+ | 99.85% |
| Horsepower | |
| Residue Compression | 21,210 |
| Utility Heat, MBTU/Hr | |
| Deethanizer Reboiler | 22,298 |

*(Based on un-rounded flow rates)

DESCRIPTION OF CO-PENDING PATENT APPLICATION

Figure 2:
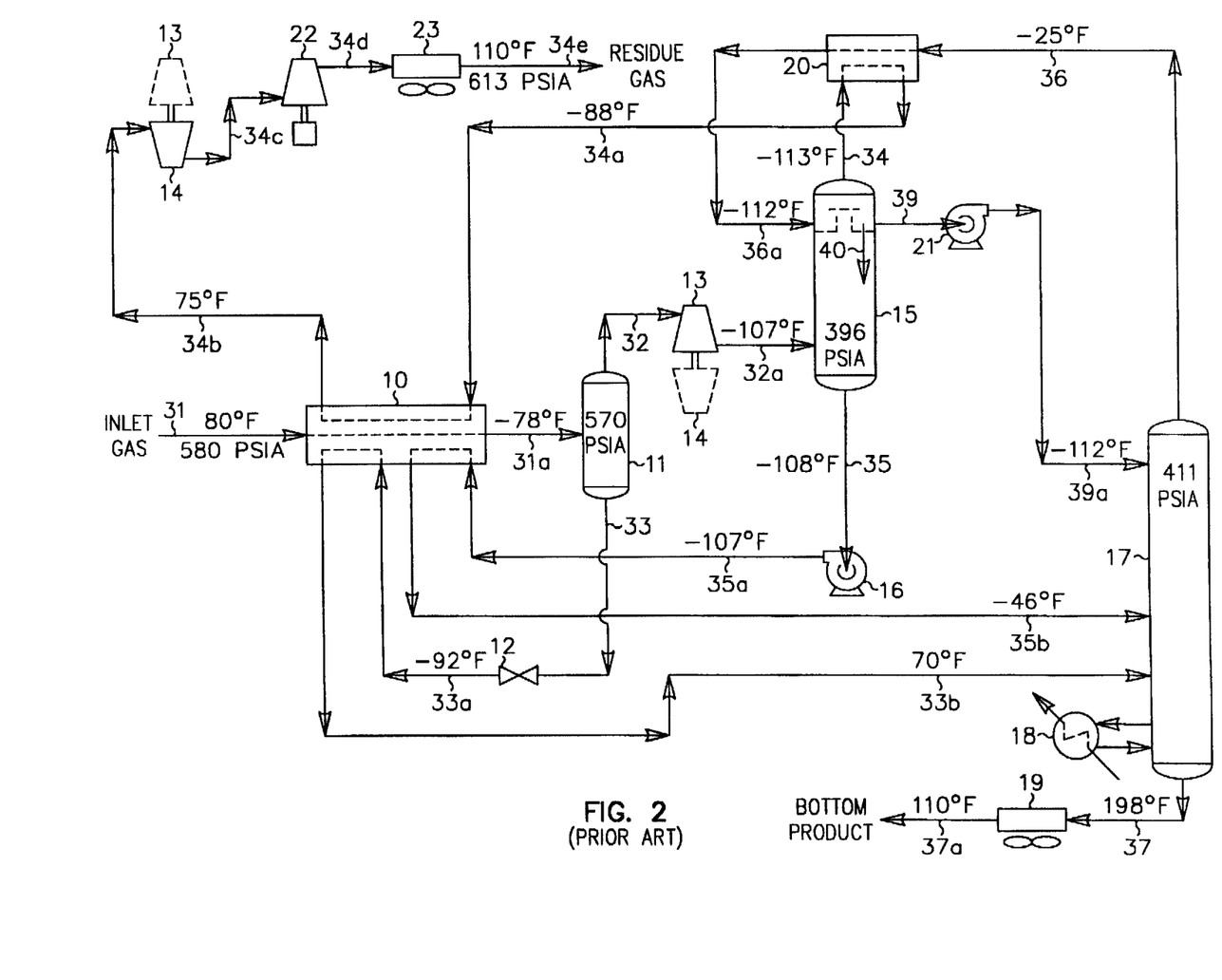
FIG. 2 is a flow diagram of a cryogenic expansion natural gas processing plant of an alternative system in accordance with co-pending U.S. patent application No. 08/696,114.

One improvement to the prior art process described above which has been disclosed in co-pending U.S. patent application No. 08/696,114 is shown in FIG. 2. The feed gas composition and conditions considered in the process presented in FIG. 2 are the same as those in FIG. 1.

In the simulation of the FIG. 2 process, feed gas enters at 80° F. and a pressure of 580 psia as stream 31. The feed stream 31 is cooled in exchanger 10 by heat exchange with cool residue gas at −88° F. (stream 34a), with separator liquids at −92° F. (stream 33a), and with separator/absorber liquids at −107° F. (stream 35a). The cooled stream 31a enters separator 11 at −78° F. and 570 psia where the vapor (stream 32) is separated from the condensed liquid (stream 33).

The vapor (stream 32) from separator 11 enters a work expansion machine 13 in which mechanical energy is extracted from this portion of the high pressure feed. The machine 13 expands the vapor substantially isentropically from a pressure of about 570 psia to a pressure of about 396 psia (the operating pressure of separator/absorber 15), with the work expansion cooling the expanded stream 32a to a temperature of approximately −107° F. The expanded and partially condensed stream 32a enters the lower section of separator/absorber 15. The liquid portion of the expanded stream commingles with liquids falling downward from the absorbing section and the combined liquid stream 35 exits the bottom of separator/absorber 15 at −108° F. The vapor portion of the expanded stream rises upward through the absorbing section and is contacted with cold liquid falling downward to condense and absorb the propane and heavier components.

The combined liquid stream 35 from the bottom of the separator/absorber 15 is routed to heat exchanger 10 by pump 16 where it (stream 35a) is heated as it provides cooling of the incoming feed gas as described earlier. The combined liquid stream is heated to −46° F., partially vaporizing stream 35b before it is supplied as a mid-column feed to deethanizer 17. The separator liquid (stream 33) is flash expanded to slightly above the 411 psia operating pressure of deethanizer 17 by expansion value 12, cooling stream 33 to −92° F. (stream 33a) before it provides cooling to the incoming feed gas as described earlier. Stream 33b, now at 70° F., then enters deethanizer 17 at a lower mid-column feed point. In the deethanizer, streams 35b and 33b are stripped of their methane and $C_2$ components. The resulting liquid product stream 37 exits the bottom of the deethanizer at 198° F. and is cooled to 110° F. (stream 37a) in heat exchanger 19 before flowing to storage.

The operating pressure is deethanizer 17 is maintained slightly above the operating pressure of separator/absorber 15. This allows the deethanizer overhead vapor (stream 36) to pressure flow through heat exchanger 20 and thence into the upper section of separator/absorber 15. In heat exchanger 20, the deethanizer overhead at −25° F. is directed in heat exchange relation with the overhead (stream 34) from separator/absorber 15, cooling the stream to −112° F. (stream 36a) and partially condensing it. The partially condensed stream is then supplied to the separator section in separator/absorber tower 15 where the condensed liquid is separated from the uncondensed vapor. The uncondensed vapor combines with the vapor rising from the lower absorbing section to form the cold distillation stream 34 leaving the upper region of separator/absorber 15. The condensed liquid is divided into two portions. One portion, stream 40, is routed to the lower absorbing section of separator/absorber 15 as the cold liquid that contacts the vapors rising upward through the absorbing section. The other portion, stream 39, is supplied to deethanizer 17 as reflux by pump 21, with reflux stream 39a flowing to a top feed point on deethanizer 17 at −112° F.

The distillation stream leaving the top of separator/absorber 15 at −113° F. is the cold residue gas stream 34. The residue gas stream passes countercurrently to deethanizer overhead stream 36 in heat exchanger 20 and is warmed to −88° F. stream 34a) as it provides cooling and partial condensation of the deethanizer overhead stream. The residue gas is further warmed to 75° F. (stream 34b) as it passes countercurrently to the incoming feed gas in heat exchanger 10. The residue gas is then re-compressed in two stages. The first stage is compressor 14 driven by expansion machine 13. The second stage is compressor 22 driven by a supplemental power source which compresses the residue gas (stream 34d) to sales line pressure. After cooling in discharge cooler 23, the residue gas product (stream 34e) flows to the sales gas pipeline at 110° F. and 613 psia.

A summary of stream flow rates and energy consumption for the process illustrated in FIG. 2 is set forth in the table below:

TABLE II (FIG. 2)
Stream Flow Summary - (Lb. Moles/Hr)

| Stream | Methane | Ethane | Propane | Butanes+ | Total |
|---|---|---|---|---|---|
| 31 | 81340 | 4128 | 878 | 439 | 87840 |
| 32 | 80084 | 3656 | 549 | 117 | 85436 |
| 33 | 1256 | 472 | 329 | 322 | 2404 |
| 35 | 2277 | 1139 | 597 | 117 | 4182 |
| 36 | 4378 | 2084 | 135 | 0 | 6695 |
| 40 | 2676 | 1549 | 102 | 0 | 4395 |
| 39 | 845 | 489 | 32 | 0 | 1388 |
| 34 | 81340 | 4112 | 55 | 0 | 86561 |
| 37 | 0 | 16 | 823 | 439 | 1279 |

| Recoveries* | |
|---|---|
| Propane | 93.68% |
| Butanes+ | 100.00% |
| Horsepower | |
| Residue Compression | 17,536 |
| Utility Heat, MBTU/Hr | |
| Deethanizer Reboiler | 16,270 |

*(Based on un-rounded flow rates)

Figure 3:
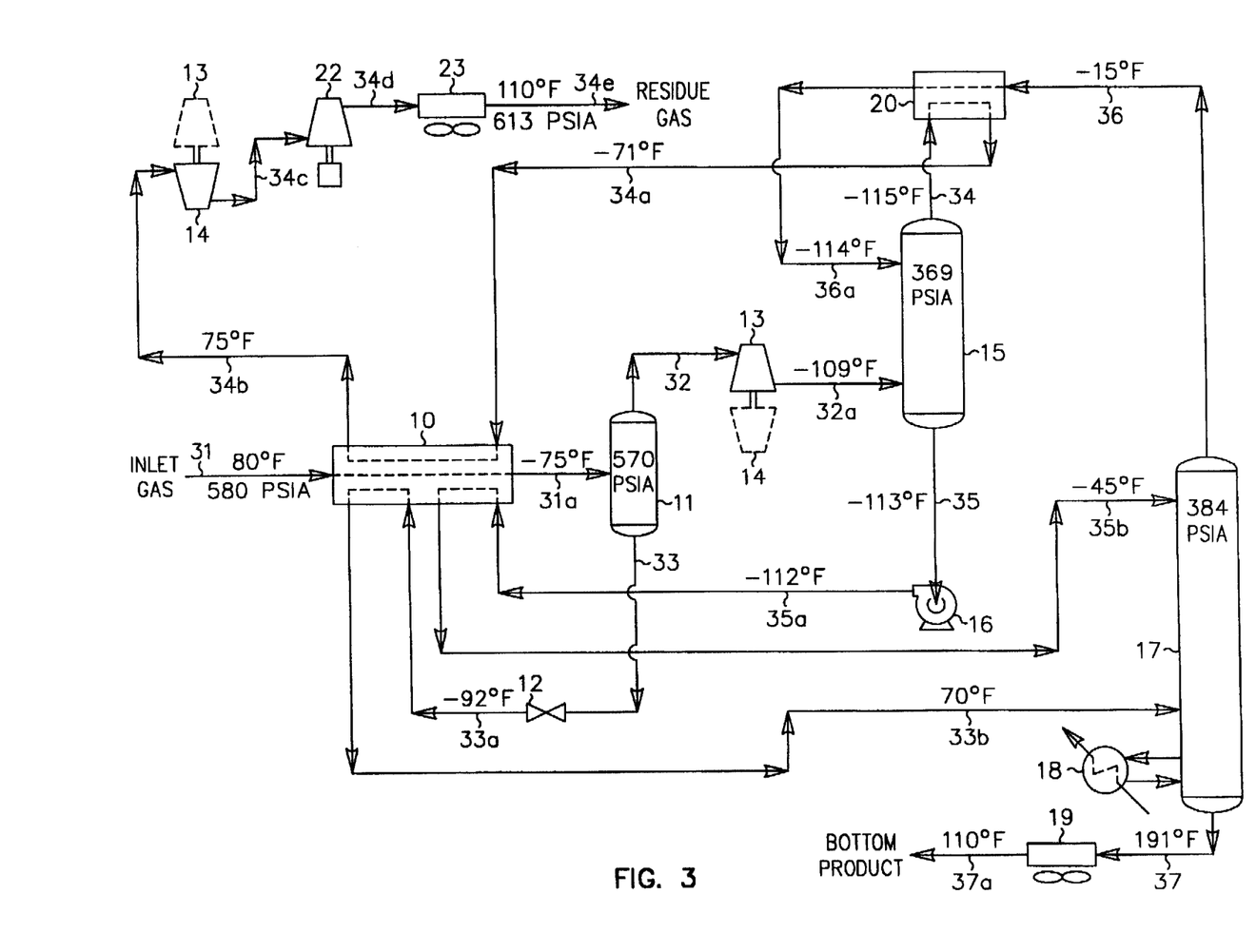
FIG. 3 is a flow diagram of a cryogenic expansion natural gas processing plant of a second alternate system in accordance with co-pending U.S. patent application No. 08/696,114.

Another improvement to the prior art process of FIG. 1 above which is also disclosed in co-pending patent application No. 06/696,114 is shown in FIG. 3. The feed gas composition and conditions considered in the process presented in FIG. 3 are the same as those in FIGS. 1 and 2.

In the simulation of the FIG. 3 process, the feed gas cooling and expansion scheme is essentially the same as that used in FIG. 2. The difference lies in the disposition of the combined liquid stream from separator/absorber 15 after it has been partially warmed (stream 35b) by providing cooling of the incoming feed gas in heat exchanger 10. Referring to FIG. 3, stream 35a from pump 16 is heated from −112° F. to −45° F. in heat exchanger 10 as it provides cooling of the incoming feed gas as described previously for FIG. 2. The heated stream, stream 35b, is then supplied to deethanizer 17 at a top column feed point, entering the tower at −45° F. to be stripped of its methane and $C_2$ components. The resulting liquid product stream 37 exits the bottom of the deethanizer at 191° F. and is cooled to 110° F. (stream 37a) in heat exchanger 19 before flowing to storage.

The operating pressure in deethanizer 17 is maintained slightly above the operating pressure of separator/absorber 15. This allows the deethanizer overhead vapor (stream 36) to pressure flow through heat exchanger 20 and thence into the upper section of separator/absorber 15. In heat exchanger 20, the deethanizer overhead at −15° F. is directed in heat exchange relation with the overhead (stream 34) from separator/absorber 15, cooling the stream to −114° F. (stream 36a) and partially condensing it. The partially condensed stream is then supplied to the separator section in separator/absorber tower 15, so that its condensed liquid is separated to become the cold liquid that contacts the vapors rising upward through the absorbing section.

The distillation stream leaving the top of separator/absorber 15 at −115° F. is the cold residue gas stream 34. The residue gas stream passes countercurrently to deethanizer overhead stream 36 in heat exchanger 20 and is warmed to −71° F. (stream 34a) as it provides cooling and partial condensation of the deethanizer overhead stream. The residue gas is further warmed to 75° F. (stream 34b) as it passes countercurrently to the incoming feed gas in heat exchanger 10. The residue gas is then re-compressed in two stages. The first stage is compressor 14 driven by expansion machine 13. The second stage is compressor 22 driven by a supplemental power source which compresses the residue gas (stream 34d) to sales line pressure. After cooling in discharge cooler 23, the residue gas product (stream 34e) flows to the sales gas pipeline at 110° F. and 613 psia.

A summary of stream flow rates and energy consumptions for the process illustrated in FIG. 3 is set forth in the table below:

TABLE III (FIG. 3)
Stream Flow Summary - (Lb. Moles/Hr)

| Stream | Methane | Ethane | Propane | Butanes+ | Total |
|---|---|---|---|---|---|
| 31 | 81340 | 4128 | 878 | 439 | 87840 |
| 32 | 80347 | 3746 | 596 | 137 | 85861 |
| 33 | 993 | 382 | 282 | 302 | 1979 |
| 35 | 4995 | 2983 | 826 | 153 | 9080 |
| 36 | 5988 | 3349 | 285 | 17 | 9781 |
| 34 | 81340 | 4112 | 55 | 0 | 86562 |
| 37 | 0 | 16 | 823 | 439 | 1278 |

| Recoveries* | |
|---|---|
| Propane | 93.68% |
| Butanes+ | 99.83% |
| Horsepower | |
| Residue Compression | 20,215 |
| Utility Heat, MBTU/Hr | |
| Deethanizer Reboiler | 20,254 |

*(Based on un-rounded flow rates)

All three of the process schemes described above utilize two fractionation towers, absorber/separator 15 and deethanizer 17, to achieve the absorption cooling effect that occurs inside absorber/separator 15, wherein the saturation of the vapors rising upward through the tower by vaporization of liquid methane and ethane contained in stream 36a provides refrigeration to the tower. (Note that, as a result, both the vapor leaving the overhead of the tower and the liquids leaving the bottom of the tower are colder than the respective feed streams at those ends of the tower. This absorption cooling effect allows the tower overhead (stream 34) to provide the cooling needed in heat exchanger 20 to partially condense the deethanizer overhead (stream 36) without operating deethanizer 17 at a pressure significantly higher than that of the separator/absorber 15.) However, two towers are required to provide the pressure driving force for flow of deethanizer 17 overhead stream 36 through exchanger 20 and to the top feed position of the absorber/separator. Typically this top feed, stream 36a, is not totally condensed and the vapor portion of it simply combines with the vapor flowing upward from absorber section 15b to form the cold residue, stream 34. The uncondensed portion of stream 36a, therefore, does not contribute to the absorption cooling inside absorber/separator 15.

DESCRIPTION OF THE INVENTION

EXAMPLE 1

Figure 4:
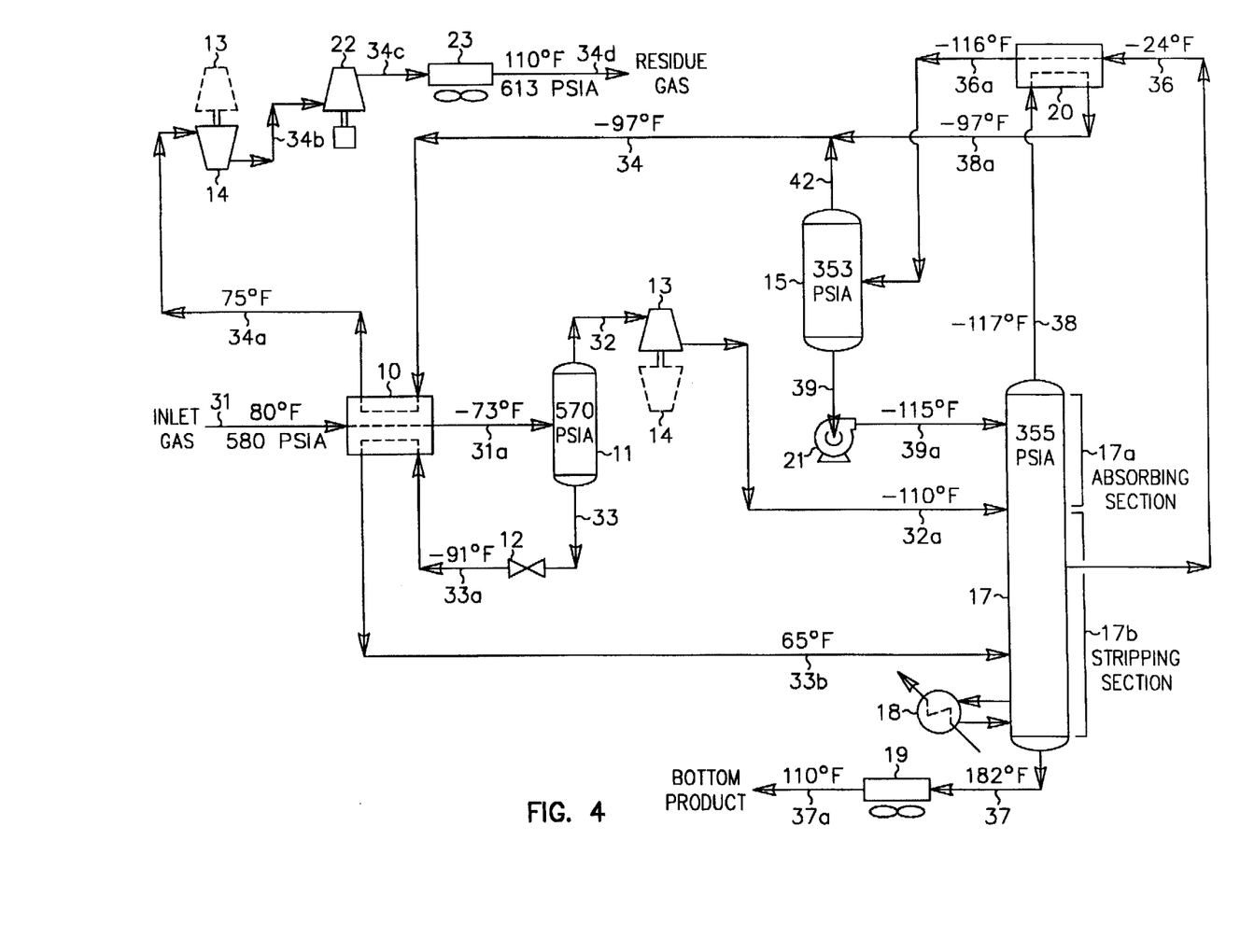
FIG. 4 is a flow diagram of a natural gas processing plant in accordance with the present invention.

FIG. 4 illustrates a flow diagram of a process in accordance with application of the present invention to the process of FIG. 1. The feed gas composition and conditions considered in the process presented in FIG. 4 are the same as those in FIG. 1. Accordingly, the FIG. 4 process can be compared with that of the FIG. 1 process to illustrate the advantages of the present invention.

In the simulation of the FIG. 4 process, feed gas enters at 80° F. and a pressure of 580 psia as stream 31. The feed stream 31 is cooled in exchanger 10 by heat exchange with cool residue gas at −97° F. (stream 34) and separator liquids at −91° F. (stream 33a). The cooled stream 31a enters separator 11 at −73° F. and 570 psia where the vapor (stream 32) is separated from the condensed liquid (stream 33).

The vapor (stream 32) from separator 11 enters a work expansion machine 13 in which mechanical energy is extracted from this portion of the high pressure feed. The machine 13 expands the vapor substantially isentropically from a pressure of about 570 psia to a pressure of about 355 psia (the operating pressure of deethanizer 17), with the work expansion cooling the expanded stream 32a to a temperature of approximately −110° F. The expanded and partially condensed stream 32a enters deethanizer 17 at an upper mid-column feed position.

The deethanizer in tower 17 is a conventional distillation column containing a plurality of vertically spaced trays, one or more packed beds, or some combination of trays and packing. The deethanizer tower consists of two sections: an upper absorbing (rectification) section 17a that contains the trays and/or packing to provide the necessary contact between the vapor portion of the expanded stream 32a rising upward and cold liquid falling downward to condense and absorb the propane and heavier components; and a lower, stripping section 17b that contains the trays and/or packing to provide the necessary contact between the liquids falling downward and the vapors rising upward. The deethanizing section 17b also includes a reboiler 18 which heats and vaporizes a portion of the liquid at the bottom of the column to provide the stripping vapors which flow up the column to strip the liquid product, stream 37, of methane and $C_2$ components. Stream 32a enters deethanizer 17 at an upper mid-column feed position located in the lower region of absorbing section 17a of deethanizer 17. The liquid portion of the expanded stream commingles with liquids falling downward from the absorbing section 17a and the combined liquid continues downward into the stripping section 17b of deethanizer 17. The vapor portion of the expanded stream rises upward through the absorbing section and is contacted with cold liquid falling downward to condense and absorb the propane and heavier components.

A portion of the distillation vapor (stream 36) is withdrawn from the upper region of stripping section 17b. This stream is then cooled and partially condensed (stream 36a) in exchanger 20 by heat exchange with cold deethanizer overhead stream 38 which exits the top of deethanizer 17 at −117° F. The cold deethanizer overhead stream is warmed to approximately −97° F. as it cools stream 36 from −24° F. to about −116° F. (stream 36a).

The operating pressure in reflux separator 15 is maintained slightly below the operating pressure of deethanizer 17. This allows distillation vapor stream 36 to pressure flow through heat exchanger 20 and thence into the reflux separator 15 wherein the condensed liquid (stream 39) is separated from the uncondensed vapor (stream 42). The uncondensed vapor stream 42 combines with the warmed deethanizer overhead stream 38a from exchanger 20 to form cool residue gas stream 34.

The liquid stream 39 from reflux separator 15 is pumped by pump 21 to a pressure slightly above the operating pressure of deethanizer 17 and the stream (39a) is then supplied as cold top column feed (reflux) to deethanizer 17. This cold liquid feed (reflux) provides the same absorption cooling effect in absorbing (rectification) section 17a of deethanizer 17 as in absorber/separator 15 of the FIG. 1 process while it absorbs and condenses the propane and heavier components flowing upward from below.

In the stripping section 17b of deethanizer 17, the feed streams are stripped of their methane and $C_2$ components. The resulting liquid product stream 37 exits the bottom of the deethanizer at 182° F. and is cooled to 110° F. (stream 37a) in heat exchanger 19 before flowing to storage.

The cool residue gas stream 34 is warmed to 75° F. (stream 34a) as it passes countercurrently to the incoming feed gas in heat exchanger 10. The residue gas is then re-compressed in two stages. The first stage is compressor 14 driven by expansion machine 13. The second stage is compressor 22 driven by a supplemental power source which compresses the residue gas (stream 34c) to sales line pressure. After cooling in discharge cooler 23, the residue gas product (stream 34d) flows to the sales gas pipeline at 110° F. and 613 psia.

A summary of stream flow rates and energy consumption for the process illustrated in FIG. 4 is set forth in the table below:

TABLE IV (FIG. 4)
Stream Flow Summary - (Lb. Moles/Hr)

| Stream | Methane | Ethane | Propane | Butanes+ | Total |
|---|---|---|---|---|---|
| 31 | 81340 | 4128 | 878 | 439 | 87840 |
| 32 | 80447 | 3782 | 616 | 146 | 86029 |
| 33 | 893 | 346 | 262 | 293 | 1811 |
| 36 | 3130 | 1604 | 117 | 7 | 4930 |
| 42 | 932 | 49 | 0 | 0 | 991 |
| 39 | 2198 | 1555 | 117 | 7 | 3939 |
| 38 | 80408 | 4062 | 52 | 0 | 85569 |
| 34 | 81340 | 4111 | 52 | 0 | 86560 |
| 37 | 0 | 17 | 826 | 439 | 1280 |

| Recoveries* | |
|---|---|
| Propane | 93.96% |
| Butanes+ | 100.00% |
| Horsepower | |
| Residue Compression | 21,210 |
| Utility Heat, MBTU/Hr | |
| Deethanizer Reboiler | 22,060 |

*(Based on un-rounded flow rates)

In essence, the FIG. 4 process allows the vapor portion of stream 36a in the FIG. 1 process to bypass exchanger 20, making it possible to integrate the absorbing section 15b of the absorber/separator 15 of the FIG. 1 process into the deethanizer 17 of the FIG. 4 process as absorbing section 17a. While this reduces slightly (relative to the amount of stream 34 in the FIG. 1 process) the amount of deethanizer overhead stream 38 which flows to heat exchanger 20 in the FIG. 4 process, it allows absorbing section 17a and stripping section 17b to operate at essentially the same pressure. This provides more favorable vapor-liquid equilibrium in the column which more than offsets the slight loss of cooling in exchanger 20. In fact, comparison of the values displayed in Table I for the FIG. 1 process with those displayed in Table IV for the FIG. 4 process shows that the FIG. 4 process achieves 0.3 percentage points better propane recovery than the FIG. 1 process at the same residue compression horsepower. At the same time, the FIG. 4 process reduces the plant capital cost considerably. The two fractionation towers of the FIG. 1 process are combined into a single tower in the FIG. 4 process which saves on equipment and installation cost. In addition, reflux separator 15 of the FIG. 4 process is smaller in diameter than the top separator section 15a of absorber/separator 15 of the FIG. 1 process, which provides further savings.

EXAMPLE 2

Figure 5:
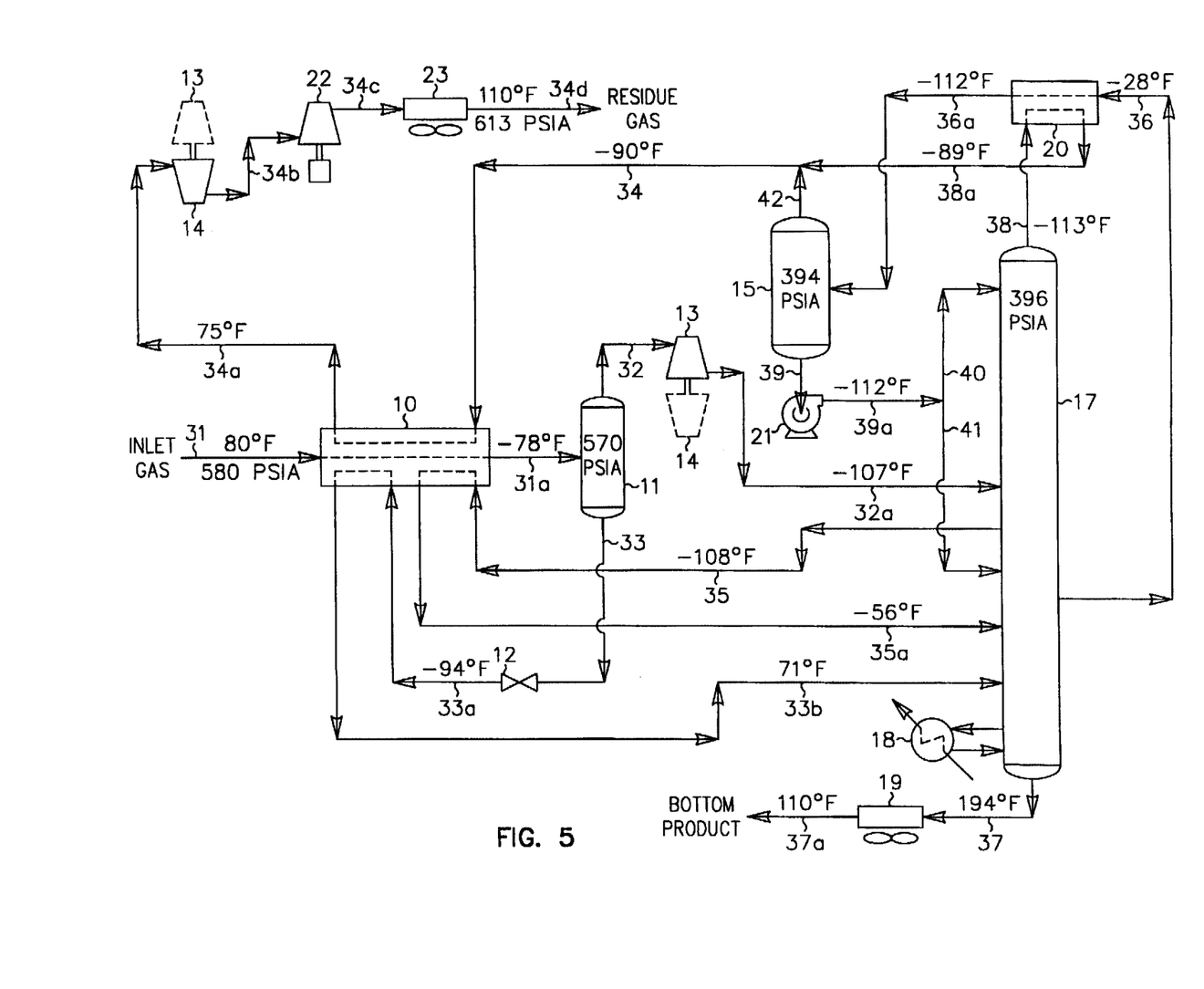
FIG. 5 is a flow diagram illustrating an alternative means of application of the present invention to a natural gas stream.

FIG. 5 illustrates a flow diagram of a process in accordance with application of the preferred embodiment of the present invention to the process of FIG. 2. The feed gas composition and conditions considered in the process presented in FIG. 5 are the same as those in FIG. 2. Accordingly, the FIG. 5 process can be compared with that of the FIG. 2 process to illustrate the advantages of the present invention.

In the simulation of the FIG. 5 process, feed gas enters at 80° F. and a pressure of 580 psia as stream 31. The feed stream 31 is cooled in exchanger 10 by heat exchange with cool residue gas at −90° F. (stream 34), with separator liquids at −94° F. (stream 33a), and with deethanizer liquids at −108° F. (stream 35). The cooled stream 31a enters separator 11 at −78° F. and 570 psia where the vapor (stream 32) is separated from the condensed liquid (stream 33).

The vapor (stream 32) from separator 11 enters a work expansion machine 13 in which mechanical energy is extracted from this portion of the high pressure feed. The machine 13 expands the vapor substantially isentropically from a pressure of about 570 psia to a pressure of about 396 psia (the operating pressure of deethanizer 17), with the work expansion cooling the expanded stream 32a to a temperature of approximately −107° F. The expanded and partially condensed stream 32a enters the lower portion of the absorbing (rectification) section of deethanizer 17. The liquid portion of the expanded stream commingles with liquids falling downward from the absorbing section and the combined liquid proceeds downward into the stripping section of deethanizer 17. The vapor portion of the expanded stream rises upward through the absorbing section and is contacted with cold liquid falling downward to condense and absorb the propane and heavier components.

A liquid stream 35 from deethanizer 17 is withdrawn from the upper region of stripping section 17b and is routed to heat exchanger 10 where it is heated as it provides cooling of the incoming feed gas as described earlier. Typically the flow of this liquid from the deethanizer is via thermosiphon circulation, but a pump could be used. The liquid stream is heated to −56° F., partially vaporizing stream 35a before it is returned as a mid-column feed to deethanizer 17, typically in the middle region of the stripping section.

The separator liquid (stream 33) is flash expanded to slightly above the 396 psia operating pressure of deethanizer 17 by expansion valve 12, cooling stream 33 to −94° F. (stream 33a) before it provides cooling to the incoming feed gas as described earlier. Stream 33b, now at 71° F., then enters deethanizer 17 at a lower mid-column feed point. In the deethanizer, streams 35a and 33b are stripped of the methane and $C_2$ components. The resulting liquid product stream 37 exits the bottom of the deethanizer at 194° F. and is cooled to 110° F. (stream 37a) in heat exchanger 19 before flowing to storage.

A portion of the distillation vapor (stream 36) is withdrawn from the upper region of the stripping section in deethanizer 17. This stream is then cooled and partially condensed (stream 36a) by heat exchange with cold deethanizer overhead vapor stream 38 which exits the top of deethanizer 17 at a temperature of about −113° F. The deethanizer overhead stream is warmed to approximately −89° F. as it cools stream 36 from −28° F. to about −112° F. (stream 36a).

The operating pressure in deethanizer 17 is maintained slightly above the operating pressure of reflux separator 15. This allows distillation vapor stream 36 to pressure flow through heat exchanger 20 and thence into reflux separator 15 wherein the condensed liquid (stream 39) is separated from the uncondensed vapor (stream 42). The uncondensed vapor combines with the warmed deethanizer overhead stream 38a from exchanger 20 to form the cool residue gas stream 34. The condensed liquid (stream 39) is pumped by pump 21 to a pressure slightly above the operating pressure of deethanizer 17. The pumped stream 39a is then divided into at least two portions. One portion, stream 40, is routed as top feed (reflux) to deethanizer 17 as the cold liquid that contacts the vapors rising upward through the absorbing (rectification) section. The other portion, stream 41, is supplied to deethanizer 17 at a mid-column feed position located in the upper region of the stripping section to provide partial rectification of distillation vapor stream 36.

The cool residue gas stream 34 is warmed to 75° F. (stream 34a) as it passes countercurrently to the incoming feed gas in heat exchanger 10. The residue gas is then re-compressed in two stages. The first stage is compressor 14 driven by expansion machine 13. The second stage is compressor 22 driven by a supplemental power source which compresses the residue gas (stream 34c) to sales line pressure. After cooling in discharge cooler 23, the residue gas product (stream 34d) flows to the sales gas pipeline at 110° F. and 613 psia.

A summary of stream flow rates and energy consumption for the process illustrated in FIG. 5 is set forth in the table below:

TABLE V (FIG. 5)
Stream Flow Summary - (Lb. Moles/Hr)

| Stream | Methane | Ethane | Propane | Butanes+ | Total |
|--------|---------|--------|---------|----------|-------|
| 31 | 81340 | 4128 | 878 | 439 | 87840 |
| 32 | 80065 | 3650 | 546 | 116 | 85407 |
| 33 | 1275 | 478 | 332 | 323 | 2433 |
| 35 | 2241 | 1114 | 583 | 120 | 4105 |
| 36 | 4289 | 2019 | 113 | 0 | 6516 |
| 42 | 845 | 44 | 1 | 0 | 898 |
| 39 | 3444 | 1975 | 112 | 0 | 5618 |
| 40 | 2669 | 1531 | 87 | 0 | 4354 |
| 41 | 775 | 444 | 25 | 0 | 1264 |
| 38 | 80495 | 4068 | 49 | 9 | 85659 |
| 34 | 81340 | 4112 | 50 | 0 | 86557 |
| 37 | 0 | 16 | 828 | 439 | 1283 |

| Recoveries* | |
|---|---|
| Propane | 94.24% |
| Butanes+ | 100.00% |
| Horsepower | |
| Residue Compression | 17,534 |
| Utility Heat, MBTU/Hr | |
| Deethanizer Reboiler | 16,000 |

*(Based on un-rounded flow rates)

Comparison of the values displayed in Table II for the FIG. 2 process with those displayed in Table V for the FIG. 5 process shows again that by allowing the vapor portion of stream 36a in the FIG. 2 process to bypass exchanger 20, the fractionation provided by absorber/separator 15 and deethanizer 17 in the FIG. 2 process can be combined into a single column, deethanizer 17 in the FIG. 5 process. By using a side liquid draw from the column to provide partial inlet gas cooling in exchanger 10 and by splitting in liquid stream 39a from reflux separator 15 into two deethanizer feeds, the same improvement in product recovery and energy utilization can be realized as in the FIG. 2 process. In fact, because the fractionation occurs in a single column, the column can be operated at a lower pressure resulting in more favorable vapor-liquid equilibrium. This yields an increase in product recovery for this case of 0.56 percentage points at essentially the same recompression power requirement and at a lower deethanizer reboiler duty relative to the FIG. 2 process. As in Example 1 above, this single fractionation column system will provide considerable capital cost savings. In addition, compared to the FIG. 2 process, the single fractionation column eliminates the absorber/separator pump for further capital and utility savings.

Comparison of the values in Tables IV and V for the FIG. 4 and FIG. 5 processes shows the advantages of the FIG. 5 embodiment of the present invention over the FIG. 4 embodiment. The split reflux streams (streams 40 and 41) of the FIG. 5 embodiment allow both rectification of deethanizer overhead stream 38 and partial rectification of distillation vapor stream 36, reducing the amount of $C_3$ and heavier components in both streams compared to the FIG. 4 embodiment. The result is 0.28 percentage points higher propane recovery for the FIG. 5 embodiment using 17% less residue compression power and 27% less deethanizer reboiler duty than the FIG. 4 embodiment. Accordingly, FIG. 5 is the preferred embodiment of the present invention.

EXAMPLE 3

Figure 6:
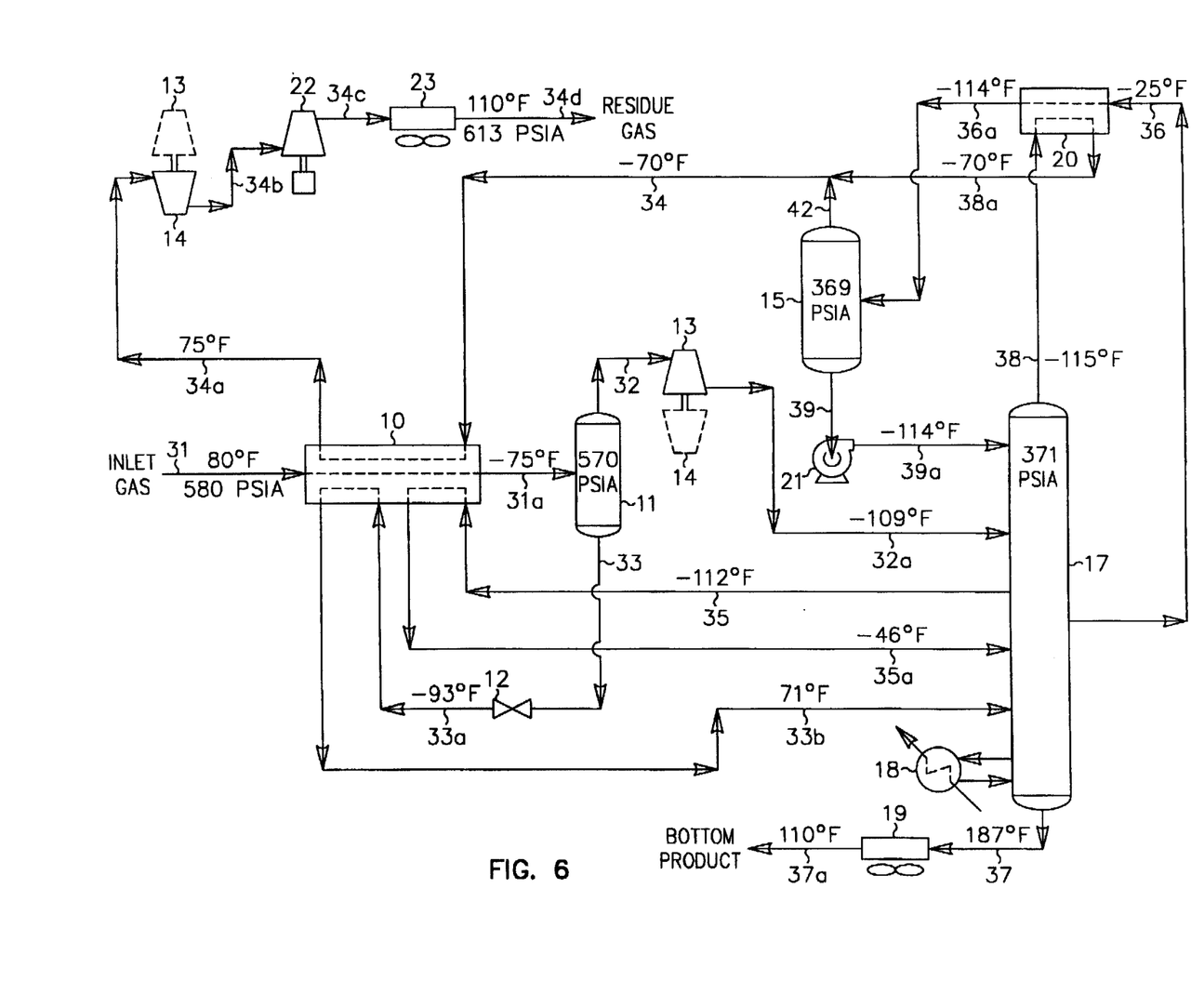
FIG. 6 is a flow diagram illustrating another alternative means of application of the present invention to a natural gas stream.

FIG. 6 illustrates a flow diagram of a process in accordance with application of the present invention to the process of FIG. 3. The feed gas composition and conditions considered in the process presented in FIG. 6 are the same as those in FIG. 3. Accordingly, the FIG. 6 process can be compared with that of the FIG. 3 process to illustrate the advantages of the present invention.

In the simulation of the FIG. 6 process, feed gas enters at 80° F. and a pressure of 580 psia as stream 31. The feed stream 31 is cooled in exchanger 10 by heat exchange with cool residue gas at −70° F. (stream 34), with separator liquids at −93° F. (stream 33a), and with deethanizer liquids at −112° F. (stream 35). The cooled stream 31a enters separator 11 at −75° F. and 570 psia where the vapor (stream 32) is separated from the condensed liquid (stream 33).

The vapor (stream 32) from separator 11 enters a work expansion machine 13 in which mechanical energy is extracted from this portion of the high pressure feed. The machine 13 expands the vapor substantially isentropically from a pressure of about 570 psia to a pressure of about 371 psia (the operating pressure of deethanizer 17), with the work expansion cooling the expanded stream 32a to a temperature of approximately −109° F. The expanded and partially condensed stream 32a enters the lower region of the absorbing (rectification) section of deethanizer 17. The liquid portion of the expanded stream commingles with liquids falling downward from the absorbing section and the combined liquid proceeds downward into the stripping section of deethanizer 17. The vapor portion of the expanded stream rises upward through the absorbing section and is contacted with cold liquid falling downward to condense and absorb the propane and heavier components.

A liquid stream 35 from deethanizer 17 is withdrawn from the upper region of the stripping section and is routed to heat exchanger 10 where it is heated as it provides cooling of the incoming feed gas as described earlier. Typically the flow of this liquid from the deethanizer is via thermosiphon circulation, but a pump could be used. The liquid stream is heated to −46° F., partially vaporizing stream 35a before it is returned as a mid-column feed to deethanizer 17, typically in the upper region of the stripping section.

The separator liquid (stream 33) is flash expanded to slightly above the 371 psia operating pressure of deethanizer 17 by expansion valve 12, cooling stream 33 to −93° F. (stream 33a) before it provides cooling to the incoming feed gas as described earlier. Stream 33b, now at 71° F., enters deethanizer 17 at a lower mid-column feed point. In the deethanizer, streams 35a and 33b are stripped of their methane and $C_2$ components. The resulting liquid product stream 37 exits the bottom of the deethanizer at 187° F. and is cooled to 110° F. (stream 37a) in heat exchanger 19 before flowing to storage.

A portion of the distillation vapor (stream 36) is withdrawn from the upper region of the stripping section in deethanizer 17. This stream is then cooled and partially condensed (stream 36a) by heat exchange with cold deethanizer overhead vapor stream 38 which exits the top of deethanizer 17 at a temperature of about −113° F. The deethanizer overhead stream is warmed to approximately −70° F. as it cools stream 36 from −25° F. to about −114° F. (stream 36a).

The operating pressure in deethanizer 17 is maintained slightly above the operating pressure of reflux separator 15. This allows distillation vapor stream 36 to pressure flow through heat exchanger 20 and thence into reflux separator 15 wherein the condensed liquid (stream 39) is separated from the uncondensed vapor (stream 42). The uncondensed vapor combines with the warmed deethanizer overhead stream 38a from exchanger 20 to form the cool residue gas stream 34. The condensed liquid (stream 39) from reflux separator 15 is pumped by pump 21 to a pressure slightly above the operating pressure of deethanizer 17. The pumped stream 39a is then routed as top feed (reflux) to deethanizer 17 as the cold liquid that contacts the vapors rising upward through the absorbing section.

The cool residue gas stream 34 is warmed to 75° F. (stream 34a) as it passes countercurrently to the incoming feed gas in head exchanger 10. The residue gas is then re-compressed in two stages. The first stage is compressor 14 driven by expansion machine 13. The second stage is compressor 22 driven by a supplemental power source which compresses the residue gas (stream 34c) to sales line pressure. After cooling in discharge cooler 23, the residue gas product (stream 34d) flows to the sales gas pipeline at 110° F. and 613 psia.

A summary of stream flow rates and energy consumption for the process illustrated in FIG. 6 is set forth in the table below:

TABLE VI (FIG. 6)
Stream Flow Summary - (Lb. Moles/Hr)

| Stream | Methane | Ethane | Propane | Butanes+ | Total |
|---|---|---|---|---|---|
| 31 | 81340 | 4128 | 878 | 439 | 87840 |
| 32 | 80336 | 3742 | 594 | 136 | 85844 |
| 33 | 1004 | 386 | 284 | 303 | 1996 |
| 35 | 5187 | 3089 | 826 | 152 | 9380 |
| 36 | 6191 | 3459 | 285 | 17 | 10097 |
| 42 | 759 | 39 | 0 | 0 | 806 |
| 39 | 5432 | 3420 | 285 | 17 | 9291 |
| 38 | 80581 | 4073 | 53 | 0 | 85755 |
| 34 | 81340 | 4112 | 53 | 0 | 86561 |

TABLE VI-continued (FIG. 6)
Stream Flow Summary - (Lb. Moles/Hr)

| 37 | 0 | 16 | 825 | 439 | 1279 |
|---|---|---|---|---|---|

| Recoveries* | |
|---|---|
| Propane | 93.86% |
| Butanes+ | 100.00% |
| Horsepower | |
| Residue Compression | 20,215 |
| Utility Heat, MBTU/Hr | |
| Deethanizer Reboiler | 19,770 |

*(Based on un-rounded flow rates)

Comparison of the values displayed in Table III for the FIG. 3 process with those displayed in Table VI for the FIG. 6 process shows again that by allowing the vapor portion of stream 36a in the FIG. 3 process to bypass exchanger 20, the fractionation provided by absorber/separator 15 and deethanizer 17 in the FIG. 3 process can be combined into a single column, deethanizer 17 in the FIG. 6 process. By using a side liquid draw from the column to provide partial inlet gas cooling in exchanger 10, the same improvement in product recovery and energy utilization can be realized as in the FIG. 3 process. Again, because the fractionation occurs in a single column, the column can be operated at a lower pressure resulting in more favorable vapor-liquid equilibrium. This yields an increase in product recovery for this case of 0.18 percentage points at essentially the same recompression power requirement and at a lower deethanizer reboiler duty relative to the FIG. 3 process. As in Example 1 above, this single fractionation column system will also provide considerable capital cost savings.

Comparison of the values in Tables IV and VI for the FIG. 4 and FIG. 6 processes shows that the FIG. 6 embodiment of the present invention can achieve essentially the same recovery levels as the FIG. 4 embodiment with slightly lower utility consumptions (residue compression power and deethanizer reboiler duty). Comparison of the values in Tables V and VI for the FIG. 5 and FIG. 6 processes shows that the FIG. 6 embodiment of the present invention cannot match the efficiency of the FIG. 5 embodiment, but the simpler arrangement of the FIG. 6 embodiment may offer capital cost advantages that outweigh its higher utility consumptions. The choice between the FIGS. 4, 5 and 6 embodiments of the present invention will often depend on factors such as plant size, available equipment, and the economic balance of capital cost versus operating cost.

OTHER EMBODIMENTS

In accordance with this invention, it is generally advantageous to design the absorbing (rectification) section of the deethanizer to contain multiple theoretical separation stages. However, the benefits of the present invention can be achieved with as few as one theoretical stage, and it is believed that even the equivalent of a fractional theoretical stage may allow achieving these benefits. For instance, all or a part of the condensed liquid (stream 39) leaving reflux separator 15 and all or a part of the partially condensed stream 32a from work expansion machine 13 can be combined (such as in the piping joining the expansion machine to the deethanizer) and if thoroughly intermingled, the vapors and liquids will mix together and separate in accordance with the relative volatilities of the various components of the total combined streams. Such commingling of the two streams shall be considered for the purposes of this invention as constituting an absorbing section.

As described earlier in the preferred embodiment (FIG. 5), the distillation vapor stream 36 is partially condensed and the resulting condensate used to absorb valuable $C_3$ components and heavier components from the vapors leaving the work expansion machine. However, the present invention is not limited to this embodiment. It may be advantageous, for instance, to treat only a portion of the outlet vapor from the work expansion machine in this manner, or to use only a portion of the condensate as an absorbent, in cases where other design considerations indicate portions of the expansion machine outlet or the condensate should bypass the absorbing section of the deethanizer. Feed gas conditions, plant size, available equipment, or other factors may indicate that elimination of work expansion machine 13, or replacement with an alternate expansion device (such as an expansion valve), is feasible, or that total (rather than partial) condensation of distillation vapor stream 36 in heat exchanger 20 is possible or is preferred. It should also be noted that, depending on the composition of the feed gas stream, it may be advantageous to use external refrigeration to provide partial cooling of the distillation vapor stream 36 in exchanger 20.

In the practice of the present invention, there will necessarily be a slight pressure difference between the deethanizer and the reflux separator which must be taken into account. If the distillation vapor stream 36 passes through heat exchanger 20 and into separator 15 without any boost in pressure, the separator shall necessarily assume an operating pressure slightly below the operating pressure of deethanizer 17. In this case, the liquid stream withdrawn from the separator can be pumped to its feed position(s) in the deethanizer. An alternative is to provide a booster blower for distillation vapor stream 36 to raise the operating pressure in heat exchanger 20 and separator 15 sufficiently so that the liquid stream 39 can be supplied to deethanizer 17 without pumping.

The use and distribution of the separator liquids, deethanizer side draw liquids, and the reflux separator liquids for process heat exchange, the particular arrangement of heat exchangers for feed gas and deethanizer feed stream cooling, and the choice of process streams for specific heat exchange services must be evaluated for each particular application. Moreover, the use of external refrigeration to supplement the cooling available to the feed gas from other process streams may be employed, particularly in the case of an inlet gas richer than that used in Example 1.

It will also be recognized that the relative amount of feed found in each branch of the condensed liquid contained in stream 39a that is split between the two column feeds in FIG. 5 will depend on several factors, including gas pressure, feed gas composition and the quantity of horsepower available. The optimum split cannot generally be predicted without evaluating the particular circumstances for a specific application of the present invention. The mid-column feed positions depicted in FIGS. 4 through 6 are the preferred feed locations for the process operating conditions described. However, the relative locations of the mid-column feeds may vary depending on inlet composition or other factors such as desired recovery levels, etc. Moreover, two or more of the feed streams, or portions thereof, may be combined depending on the relative temperatures and quantities of individual streams, and the combined stream then fed to a mid-column feed position. FIGS. 4 through 6 are the preferred embodiments for the compositions and pressure conditions shown. Although individual stream expansion is depicted in particular expansion devices, alternative expansion means may be employed where appropriate. For example, conditions may warrant work expansion of the condensed liquid stream (stream 33).

The present invention provides improved recovery of $C_1$ components per amount of utility consumption required to operate the process. It also provides for reduced capital expenditure in that all fractionation can be done in a single column. An improvement in utility consumption required for operating the deethanizer process may appear in the form of reduced power requirements for compression or re-compression, reduced power requirements for external refrigeration, reduced energy requirements for tower reboilers, or a combination thereof. Alternatively, if desired, increased $C_3$ component recovery can be obtained for a fixed utility consumption.

While there have been described what are believed to be preferred embodiments of the invention, those skilled in the art will recognize that other and further modifications may be made thereto, e.g. to adapt the invention to various conditions, types of feed or other requirements without departing from the spirit of the present invention as defined by the following claims.

We claim:

1. In a process for the separation of a gas stream containing methane, $C_2$ components, $C_3$ components and heavier hydrocarbon components into a volatile residue gas fraction containing a major portion of said methane and $C_2$ components and a relatively less volatile fraction containing a major portion of said $C_3$ components and heavier hydrocarbon components, in which process
   (a) said gas stream is treated in one or more heat exchange and/or expansion steps to partially condense at least a portion thereof and provide thereby at least a first vapor stream and at least one $C_3$-containing liquid stream which also contains lighter hydrocarbons; and
   (b) at least one of said $C_3$-containing liquid streams is directed into a distillation column wherein said liquid is separated into a second vapor stream containing predominantly methane and $C_2$ components and said relatively less volatile fraction containing the major portion of said $C_3$ components and heavier hydrocarbon components;

the improvement wherein
   (1) at least a portion of said first vapor stream is directed into a mid-column feed position on said distillation column as a second feed thereto;
   (2) a vapor distillation stream is withdrawn from a region of said distillation column below said first vapor stream and cooled sufficiently to condense at least a part of it, thereby forming a third vapor stream and a condensed stream;
   (3) at least a portion of said condensed stream is supplied to said distillation column at a top feed position;
   (4) at least a portion of said second vapor stream is directed into heat exchange relation with said vapor distillation stream, thereby to supply at least a portion of the cooling of step (2) and thereafter discharging at least a portion of said second vapor stream and said third vapor stream as said volatile residue gas fraction; and
   (6) the quantities and temperatures of said feed streams to said distillation column are effective to maintain the overhead temperature of said distillation column at a temperature whereby the major portion of said $C_3$ components and heavier hydrocarbon components is recovered in said relatively less volatile fraction.

2. The improvement according to claim 1 wherein a liquid distillation stream is withdrawn from said distillation column at a location above the region wherein said vapor distillation stream is withdrawn, whereupon said liquid distillation stream is heated and thereafter redirected into said distillation column as a third feed thereto at a location below the region wherein said vapor distillation stream is withdrawn.

3. The improvement according to claim 1 wherein
   (1) said condensed stream is divided into at least a first liquid stream and a second liquid stream;
   (2) said first liquid stream is supplied to said distillation column at a top feed position; and
   (3) said second liquid stream is supplied to said distillation column as a third feed thereto, said third feed location being in substantially the same region wherein said vapor distillation stream is withdrawn.

4. The improvement according to claim 3 wherein a liquid distillation stream is withdrawn from said distillation column at a location above the region wherein said vapor distillation stream is withdrawn, whereupon said liquid distillation stream is heated and thereafter redirected into said distillation column as a fourth feed thereto at a location below the region wherein said vapor distillation stream is withdrawn.

5. In an apparatus for the separation of a gas containing methane, $C_2$ components, $C_3$ components and heavier hydrocarbon components into a volatile residue gas fraction containing a major portion of said methane and $C_2$ components and a relatively less volatile fraction containing a major portion of said $C_3$ components and heavier hydrocarbon components, in said apparatus there being
   (a) one or more first heat exchange means and/or expansion means cooperatively connected to provide at least one partially condensed gas stream, providing thereby at least a first vapor stream and at least one $C_3$-containing liquid which also contains lighter hydrocarbons; and
   (b) a distillation column connected to receive at least one of said $C_3$-containing liquid streams which is adapted to separate said stream into a second vapor stream containing predominantly methane and $C_2$ components and said relatively less volatile fraction containing the major portion of said $C_1$ components and heavier hydrocarbon components;

the improvement wherein said apparatus includes
   (1) connecting means connected to said distillation column to supply at least a portion of said first vapor stream to said distillation column at a mid-column feed position;
   (2) vapor withdrawing means connected to said distillation column to receive a vapor distillation stream from a region of said distillation column below said first vapor stream;
   (3) second heat exchange means connected to said vapor withdrawing means to receive said vapor distillation stream and cool it sufficiently to condense at least a part of it;
   (4) separating means connected to said second heat exchange means to receive said partially condensed distillation stream and separate it, thereby to form a third vapor stream and a condensed stream, said separating means being further connected to said distillation column to supply at least a portion of said condensed stream to said distillation column at a top feed position;

(5) said distillation column being further connected to said second heat exchange means to direct at least a portion of said second vapor stream separated therein into heat exchange relation with said vapor distillation stream; and (6) control means adapted to regulate the quantities and temperatures of said feed streams to said distillation column to maintain the overhead temperature of said distillation column at a temperature whereby the major portion of said $C_3$ components and heavier components is recovered in said relatively less volatile fraction.

6. The improvement according to claim 5 wherein said apparatus includes (1) liquid withdrawing means connected to said distillation column to receive a liquid distillation stream from a region of said distillation column above that of said vapor withdrawing means;

(2) said first heat exchange means connected to said liquid withdrawing means to receive said liquid distillation stream and heat it; and (3) said first heat exchange means being further connected to said distillation column to supply said heated stream to said distillation column at a location below that of said vapor withdrawing means.

7. The improvement according to claim 5 wherein said apparatus includes (1) dividing means connected to said separating means to receive said condensed stream and divide it into at least first and second liquid streams, said dividing means being further connected to said distillation column to supply said first liquid stream to said distillation column at a top feed position; and (2) said dividing means being further connected to said distillation column to supply said second liquid stream to said distillation column at a location in substantially the same region as said vapor withdrawing means.

8. The improvement according to claim 7 wherein said apparatus includes (1) liquid withdrawing means connected to said distillation column to receive a liquid distillation stream from a region of said distillation column above that of said vapor withdrawing means;

(2) first heat exchange means connected to said liquid withdrawing means to receive said liquid distillation stream and heat it; and (3) said first heat exchange means being further connected to said distillation column to supply said heated stream to said distillation column at a location below that of said vapor withdrawing means.

* * * * *

UNITED STATES PATENT AND TRADEMARK OFFICE
CERTIFICATE OF CORRECTION

PATENT NO. : 5,799,507

DATED : September 1, 1998

INVENTOR(S) : Wilkinson, et al.

It is certified that error appears in the above-identified patent and that said Letters Patent is hereby corrected as shown below:

Column 1, line 50, "cop-pending" should read --co-pending--.

Column 1, line 52, "topic" should read --typical--.

Column 3, line 32, "lead" should read --leak--.

Column 3, line 51, "streams" should read --stream--.

Column 6, line 54, "F. stream 34a)" should read --F. (stream 34a)--.

Column 7, line 19, "Horsepower" should read --Horsepower--.

Column 7, line 27, "06/696,114" should read --08/696,114--.

Column 8, line 27, "Horsepower" should read --Horsepower--.

Column 10, line 39, "Horsepower" should read --Horsepower--.

Column 12, line 53, "Horsepower" should read --Horsepower--.

Column 14, line 21, "-113° F" should read -- -115° F--

Column 15, line 11, "Horsepower" should read --Horsepower--

Column 17, line 5, "$C_1$" should read --$C_3$--

UNITED STATES PATENT AND TRADEMARK OFFICE
CERTIFICATE OF CORRECTION

PATENT NO. : 5,799,507
DATED : September 1, 1998
INVENTOR(S) : Wilkinson, et. al.

It is certified that error appears in the above-identified patent and that said Letters Patent is hereby corrected as shown below:

Column 18, line 46, "$C_1$" should read --$C_3$--

Signed and Sealed this

Eighth Day of February, 2000

Attest:

Q. TODD DICKINSON

Attesting Officer

Commissioner of Patents and Trademarks